United States Patent [19]
Bearman et al.

[11] Patent Number: 6,083,158
[45] Date of Patent: Jul. 4, 2000

[54] REAL-TIME VISUALIZATION OF TISSUE ISCHEMIA

[75] Inventors: Gregory H. Bearman, Pasadena; Thomas D. Chrien, Altadena; Michael L. Eastwood, South Pasadena, all of Calif.

[73] Assignee: The United States of America as represented by the Administrator of the National Aeronautics and Space Administration, Washington, D.C.

[21] Appl. No.: 09/160,196

[22] Filed: Sep. 1, 1998

[51] Int. Cl.[7] .......................................................... A61B 5/00
[52] U.S. Cl. ............................................. 600/323; 600/476
[58] Field of Search ..................................... 600/310, 322, 600/323, 324, 340, 473, 476, 407

[56] References Cited

U.S. PATENT DOCUMENTS

| | | |
|---|---|---|
| 3,802,776 | 4/1974 | Tchang . |
| 3,994,585 | 11/1976 | Frey . |
| 4,463,762 | 8/1984 | Rubens . |
| 4,819,646 | 4/1989 | Cheung et al. . |
| 4,997,769 | 3/1991 | Lundsgaard . |
| 5,198,977 | 3/1993 | Salb ......................................... 600/310 |
| 5,318,022 | 6/1994 | Taboado et al. . |
| 5,421,337 | 6/1995 | Richards-Kortum et al. . |
| 5,515,859 | 5/1996 | Paz . |
| 5,601,080 | 2/1997 | Oppenheimer . |
| 5,747,789 | 5/1998 | Godik ....................................... 600/310 |

*Primary Examiner*—Eric F. Winakur
*Attorney, Agent, or Firm*—John H. Kusmiss

[57] ABSTRACT

A real-time display of tissue ischemia which comprises three CCD video cameras, each with a narrow bandwidth filter at the correct wavelength. The cameras simultaneously view an area of tissue suspected of having ischemic areas through beamsplitters. The output from each camera is adjusted to give the correct signal intensity for combining with the others into an image for display. If necessary, a digital signal processor (DSP) can implement algorithms for image enhancement prior to display. Current DSP engines are fast enough to give real-time display. Measurement at three wavelengths, combined into a real-time Red-Green-Blue (RGB) video display with a digital signal processing (DSP) board to implement image algorithms, provides direct visualization of ischemic areas.

12 Claims, 3 Drawing Sheets

REAL-TIME VISUALIZATION OF TISSUE ISCHEMIA

ORIGIN OF THE INVENTION

The invention described herein was made in the performance of work under a NASA contract, and is subject to the provisions of Public Law 96-517 (35 USC 202) in which the Contractor has elected not to retain title.

TECHNICAL FIELD

The present invention relates to a system and method for visualization of tissue ischemia and, more particularly, to an instrument and method for the real-time visualization of tissue ischemia.

BACKGROUND OF THE INVENTION

There are many clinical settings where the oxygen content of large areas of tissue is needed to help in identifying and/or monitoring and treatment of areas of healthy, diseased or dead tissue. Real-time identification of ischemic tissue will provide valuable information to a surgeon before and after operating on an organ. A real-time visual representation of ischemic tissue will also guide the surgeon in the selective removal of severely burned skin. Healthy tissue is retained increasing chances of survival, increasing the rate of cure and decreasing the overall period of convalescence. During surgery on an organ, areas of the tissue of the organ can become ischemic. The ischemic areas could be treated instantly if they could be localized.

LIST OF REFERENCES

| PATENT NO. | PATENTEE |
| --- | --- |
| 3,802,776 | Tchang |
| 3,994,585 | Frey |
| 4,463,762 | Rubens |
| 4,819,646 | Cheung et al. |
| 4,997,769 | Lundsgaard |
| 5,318,022 | Taboada et al. |
| 5,421,337 | Richards-Kortum et al |
| 5,515,859 | Paz |
| 5,601,080 | Oppenheimer |

STATEMENT OF THE PRIOR ART

Ischemic tissue can be identified by determining the ratio of deoxyhemoglobin to oxyhemoglobin in the blood of the tissue. Currently, determination of the deoxy/oxyhemoglobin content of blood involves in-place monitors, followed by time delayed analysis in a laboratory of Doppler oximetry. This technique does not provide results quickly enough to be used during surgery or treatment of ischemic tissue.

Other systems for determining oxygen content of blood have been disclosed in the prior art.

Taboada, et al. disclose a device that uses a laser to illuminate tissue and then calculates blood oxygen from the reflected light at three different illumination wavelengths. Imaging is through a slit lamp microscope.

Tchang does not disclose imaging. A photometer determines the oxygen content of blood at 805 and 605 nm. Tchang's method appears to require a blood sample.

Frey discloses an apparatus for determining the hemoglobin content of blood using spectral analysis in a predetermined range. The technique requires a blood sample. The technique only works in absorption, which means it cannot be used for reflection imaging; i.e., requires illumination source behind sample. Absorption measurements are fundamentally different from reflection measurements. One has to use scattering theory to transform an absorption spectrum into a reflection one.

Cheung, et al. is a refinement of pulse oximetry, a current standard technique that uses a clip-on device for fingers or ears. Pulse oximetry, widely used, does not provide any imaging information and also uses transmitted light. A feedback control system is responsive to light at two different wavelengths and is used to measure the oxygen content of hemoglobin in an oximetry system.

Lundsgaard is an analytic laboratory instrument for blood samples. The concentration of various blood components are determined using a number of spectral wavelengths.

Richards-Kortum, et al. is for optical spectroscopy of cancers and dysplasias. This is a new approach to tissue pathology for in situ detection of tumors. This patent is focused on cancer detection.

Oppenheimer and Paz both require blood for analysis. Oppenheimer in particular works on circulating blood, as in a dialysis patient.

STATEMENT OF THE INVENTION

The invention provides real-time visualization and localization of ischemic tissue within a larger area of tissue by imaging with a white light source. The technique utilizes the spectral signatures of deoxy/oxyhemoglobin and oxyhemoglobin. The technique is non-invasive, does not require contact with tissue and yields local information concerning the blood oxygen content of regions of the tissues. The invention provides a means for easily localizing and imaging specific organs providing real-time feedback during surgery and treatment.

A real-time display of tissue ischemia according to this invention comprises three Charge Coupled Device (CCD) video cameras, each with a narrow bandwidth filter at the correct wavelength. The cameras simultaneously view an area of tissue suspected of having ischemic areas through beamsplitters. The output from each camera is adjusted to give the correct signal intensity for combining with the others into an image for display. If necessary, a digital signal processor can implement algorithms for image enhancement prior to display. Current DSP engines are fast enough to give real-time display. The detector can also be a single CCD with three filtered areas providing separate colored images on the detector. The filtering can be introduced as part of the optical imaging or directly in front of the CCD.

Measurement at three wavelengths, combined into a real-time RGB video display with a digital signal processing (DSP) board to implement image algorithms, provides direct visualization of ischemic areas.

This invention can be used in any medical application requiring monitoring of blood oxygen or vascularization. Some specific applications are the localization and monitoring of burned areas of skin and other organs; monitoring blood flow of transplanted organs, especially the kidneys; localization of ischemic parts of organs for surgical resection, and diagnosis and monitoring of inflammatory bowel disease.

These and many other features and attendant advantages of the invention will become apparent as the invention becomes better understood by reference to the following detailed description when considered in conjunction with the accompanying drawings.

DETAILED DESCRIPTION OF THE INVENTION

Figure 1:
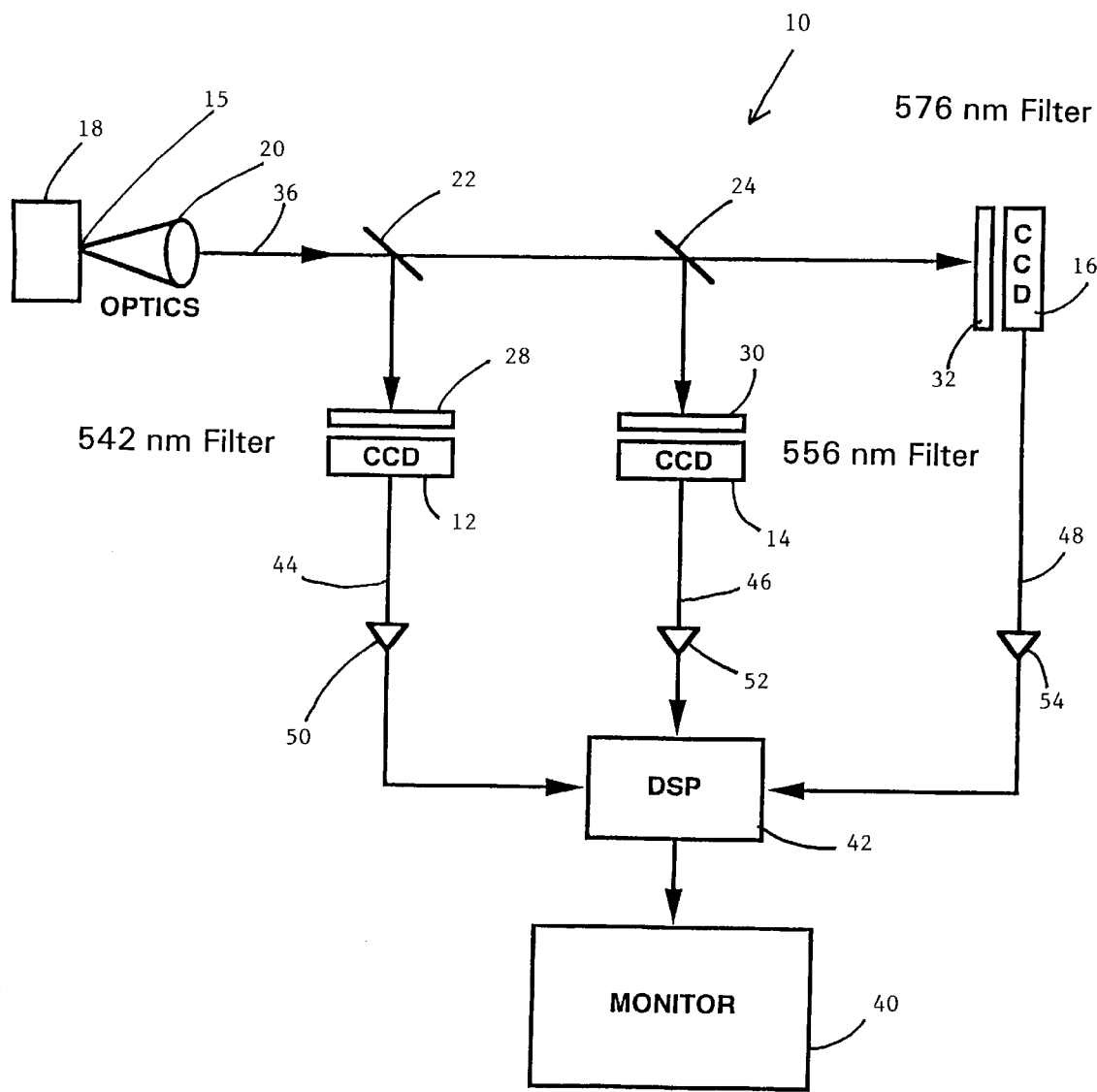
FIG. 1 is a schematic-block illustration of the system of the invention.

Referring now to FIG. 1, the real-time ischemic display system 10 of the invention includes 3 Charge Coupled Device (3CCD) video cameras 12, 14, 16. The cameras simultaneously view an area 15 on a sample of tissue 18 through optics 20. The sample is illuminated with broad band, uncollimated light source. The light 36 reflected from the sample 18 can be directed to the cameras 12, 14, 16 by a series of beam splitters 22, 24. A narrow bandwidth filter 28 at 542 nm is positioned in front of the first camera 12. A second narrow bandwidth 556 nm filter 30 is positioned before camera 14 and a third narrow bandwidth 576 nm filter 32 is positioned in front of camera 16.

Figure 2:
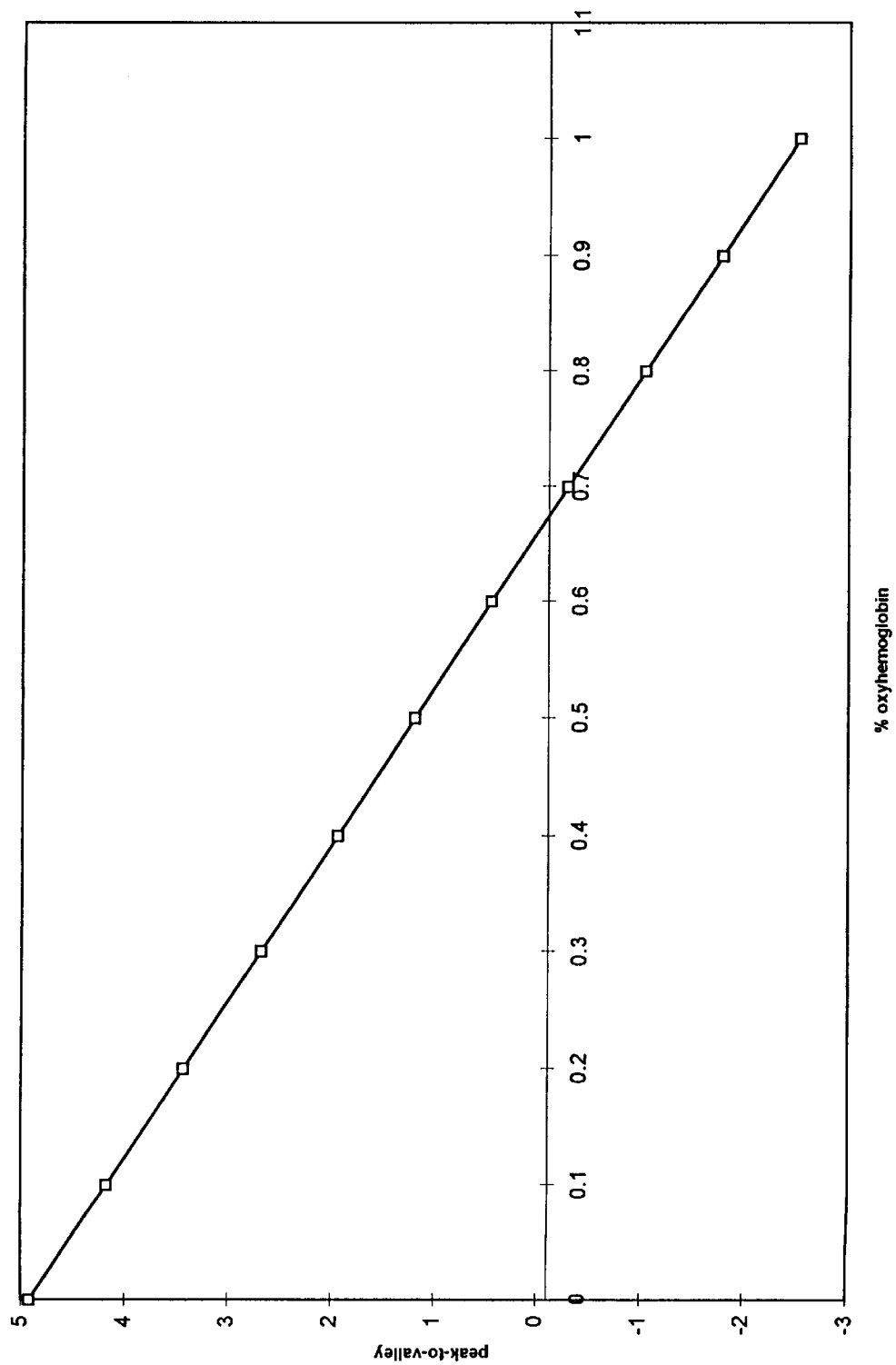
FIG. 2 is a hemoglobin algorithm with peak-to-valley plotted against percent oxyhemoglobin.
Figure 3:
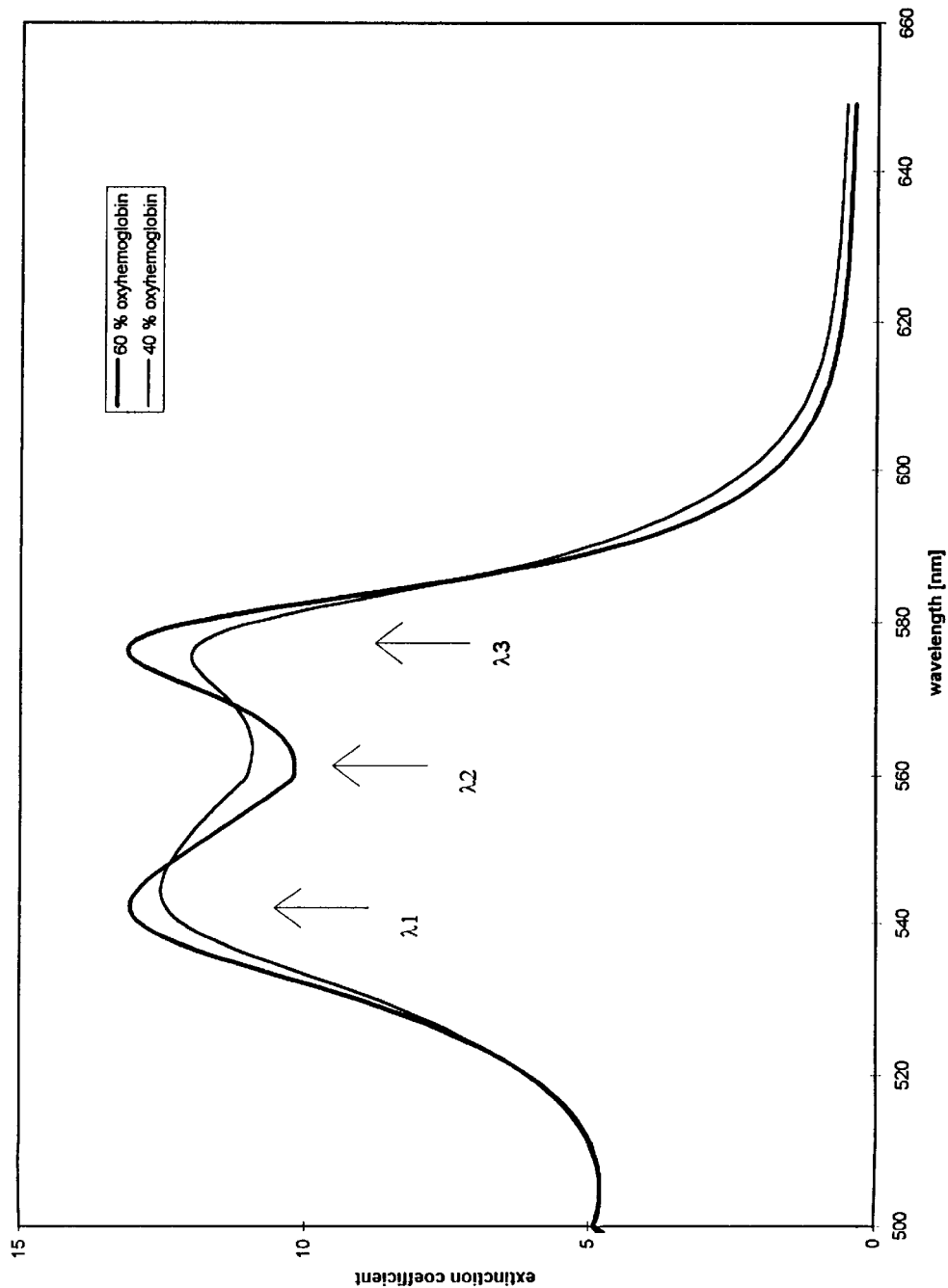
FIG. 3 is a blood spectra of blood samples containing 60% hemoglobin and 40% deoxyhemoglobin.

The filters are selected based on the absorption characteristics of oxyhemoglobin and deoxyhemoglobin. Referring now to FIGS. 2 and 3, oxyhemoglobin has absorption peaks at 542 nm and 576 nm, while deoxyhemoglobin has an absorption peak at 556 nm. As the oxyhemoglobin is converted to deoxyhemoglobin, the 542 nm and 576 nm peaks are depressed and the feature at 556 nm appears. There is another minimum in the oxyhemoglobin spectrum at 660 nm. Simultaneous color images at 542, 556 and 576 nm can be combined to enhance the spectral contrast between deoxyhemoglobin and oxyhemoglobin, thus providing a direct image of the tissue sample that shows relative blood oxygen content. This false color image, combined as a multicolor image such as red-blue-green (RGB) image, is displayed on a monitor 40. For example, the red zones could depict tissue zones of high oxygen content, blue zones could depict zones of very low oxygen content and green zones represent no oxygen present in the tissue. If necessary, a digital signal processor 42 can be utilized to process the signals 44, 46, 48 from the 3 cameras 12, 14, 16 before being fed to the monitor 40. Digital signal processing at 200–300 megahertz provides high speed numerical compilation for imaging. A variable amplifier 50, 52, 54 can be interposed between each camera 12, 14, 16 and the monitor 40.

The DSP 42 can interpret algorithms for image enhancement before the image is displayed on monitor 40.

The algorithm for hemoglobin as percent oxyhemoglobin is illustrated in FIG. 2. The three wavelengths $\lambda$, $\lambda_2$, $\lambda_3$ that are shown in FIG. 3 can be used to provide the following algorithms for mapping relative blood oxygenation. The algorithm calculates each pixel value as a measure of relative oxygen. A representative algorithm is as follows:

The algorithm measures the peak-to-valley ratio at $\lambda_2$ as follows:

$\lambda_1$ and $\lambda_3$ define a line given by $S(\lambda)=m\lambda+b$ (as shown in FIG. 2)

$m = S(\lambda_1) - S(\lambda_3)/(\lambda_1 - \lambda_3)$ $b = S(\lambda_1) - m*\lambda_1$ where $S(\lambda)$ is the signal at any wavelength.

One measure of the relative amount of oxyhemoglobin and deoxyhemoglobin is the depth of the valley at $\lambda_2$, which can be determined as follows:

$PV = S(\lambda_2) - m\lambda_2 - b$

PV can go negative, but still tracks the oxy/deoxy ratio as shown in FIG. 2.

The system of the invention provides real time processing and visualization of a sample of tissue as a 3 color image representative of blood oxygen content of the tissue. The system can be utilized to visualize the blood in arteries which usually have an oxygen content of about 90% or veins which usually have an oxygen content of about 70%.

It is to be realized that only preferred embodiments of the invention have been described and that numerous substitutions, modifications and alterations are permissible without departing from the spirit and scope of the invention as defined in the following claims.

We claim:

1. A method of displaying a multicolor map image containing at least 3 distinct colors, a first color representing high oxygen content, a second color representing low oxygen content and the third color representing absence of oxygen in an area of viewed animal tissue comprising the steps of:

illuminating the area with a non-collimated, broad band light source containing 3 preselected wavelengths, two of the wavelengths being absorption peaks of oxyhemoglobin and one of the wavelengths being an absorption peak of deoxyhemoglobin;

filtering an image reflected from the area through a set of three narrow band filters to filter light at the three preselected wavelengths to provide three distinct image signals, each having an intensity;

processing the three distinct image signals into a composite three color video image signal representative of relative blood oxygen content throughout the area of tissue; and displaying the composite signal on a video color monitor as said multicolor map image.

2. A method according to claim 1 further including the step of storing the composite signal on a video signal recording medium.

3. A method according to claim 1 further including the step of processing the three distinct image signals in a digital signal processor to form said composite signal.

4. A method according to claim 3, further including the step of controlling the intensity of each of the three, distinct, image signals before processing the three, distinct, image signals in the digital signal processor.

5. A method according to claim 1, in which the reflected image is filtered at preselected wavelengths at 542 nm, 576 nm and 556 nm, respectively.

6. A method according to claim 1 in which the area imaged has a dimension of at least 0.5 cm$^2$.

7. A method according to claim 1, in which the three distinct colors are red, blue and green indicative of high, moderate and low blood oxygen content, respectively.

8. A method according to claim 1, in which the animal is human.

9. A system for displaying a multicolor map image containing a first color representing high oxygen content, a second color representing low oxygen content and a third color representing absence of oxygen in an area of viewed animal tissue comprising in combination:

means for illuminating the area of the tissue with a non-collimated light source containing 3 preselected wavelengths;

optic means for viewing an image of the area reflected from the illuminated area;

means for filtering the viewed image at a first of the preselected wavelengths indicative of peak absorption of oxyhemoglobin to develop a first image signal;

means for filtering the viewed image at a second of the preselected wavelengths indicative of peak absorption of oxyhemoglobin to develop a second image signal;

means for filtering the viewed image at a third of the preselected wavelengths indicative of absence of deoxyhemoglobin to develop a third image signal; and video means for processing the first, second and third image signals into three video image signals in said three colors; and means for displaying the video image signals as said multicolor map image.

10. A system according to claim 9, further including an aperture device having a minimum aperture permitting reflection of an image of the tissue of an area of at least 0.5 $cm^2$.

11. A system according to claim 9, in which the first and second wavelengths are at 542 nm and 576 nm and the third wavelength is at 556 nm.

12. A system according to claim 9, in which the first, second and third colors are red, blue and green, respectively.

* * * * *